(12) United States Patent
Fyvie et al.

(10) Patent No.: US 6,268,461 B1
(45) Date of Patent: Jul. 31, 2001

(54) METHOD FOR PREPARING HYDROXYAROMATIC CHLOROFORMATES

(75) Inventors: Thomas Joseph Fyvie, Schenectady; James Manio Silva, Clifton Park, both of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/431,628

(22) Filed: Nov. 2, 1999

(51) Int. Cl.[7] .................................................. C08G 64/01
(52) U.S. Cl. ........................................... 528/196; 528/198
(58) Field of Search ...................................... 528/196, 198

(56) References Cited

U.S. PATENT DOCUMENTS

| | | | |
|---|---|---|---|
| 4,864,011 | 9/1989 | Bussink et al. | 528/198 |
| 5,274,164 | 12/1993 | Wettling et al. | 558/282 |
| 5,399,657 | 3/1995 | van Hout et al. | 528/198 |

*Primary Examiner*—Terressa M. Boykin
(74) *Attorney, Agent, or Firm*—Noreen C. Johnson; Douglas E. Stoner

(57) ABSTRACT

This invention relates to a process for the preparation of hydroxyaromatic chloroformate products suitable for use as chainstopping or endcapping agents. The process involves a semi-batch process in which an aqueous caustic solution is introduced into a vessel comprising a precharge solution, and careful control of the overall molar ratios of phosgene, caustic and hdyroxyaromatic compound are maintained.

19 Claims, No Drawings

METHOD FOR PREPARING HYDROXYAROMATIC CHLOROFORMATES

FIELD OF THE INVENTION

This invention relates to a process for preparation of hydroxyaromatic chloroformate products by an interfacial process. The hydroxyaromatic chloroformates are suitable for use as an endcapping agent in polymer synthesis. In particular, it is desirable to use the hydroxyaromatic chloroformate products as an endcapping agent in polycarbonate synthesis.

BACKGROUND OF THE INVENTION

The use of hydroxyaromatic chloroformates as a chain-stopping or endcapping agent in polycarbonate synthesis facilitates control of the molecular weight of the polycarbonate to be formed. In general, the greater the quantity of endcapping agent introduced into a polycarbonate synthesis, the lower the molecular weight of the polycarbonate product. Hydroxyaromatic chloroformates are particularly suitable as endcapping agents in interfacial polycarbonate synthesis because they produce a polycarbonate product in a single step phosgenation with a lower level of diarylcarbonate (DAC) than products produced using a hydroxyaromatic endcap, such as p-cumyl phenol. Diarylcarbonates have a low melting point, and a polycarbonate containing diaryl carbonates can lead to undesirable effects, such as "plate out" in which the DAC from previous molding cycles condenses on the mold and leads to blemishes in subsequent molding. The term "DAC" as used herein is understood to include also di(alkylphenyl carbonates) and di(arylphenyl) carbonates.

U.S. Pat. No. 5,399,657 (Van Hout et al) discloses a method of preparing hydroxyaromatic chloroformate compounds in which a solution of phosgene in a solvent is introduced into a reactor, to which phosgene and a phenol compound are then added while maintaining the temperature at the desired level by cooling, and maintaining the pH at desired levels by the addition of an aqueous caustic solution.

U.S. Pat. No. 5,274,164 (Wettling et al) discloses a method of preparing aryl chloroformates by the reaction of phenols with phosgene in the presence of organic phosphorous compounds. The addition of a catalyst, such as the organic phosphorous compounds, necessitates extra process steps to recover the catalyst from the product.

U.S. Pat. No. 4,864,011 (Bussink et al) discloses a method of preparing an aromatic polycarbonate with a phenolic chloroformate chain stopper.

It would be desirable to develop a process in which hydroxyaromatic chloroformates are produced in an interfacial process from one or more monofunctional hydroxyaromatic compounds, a carbonate precursor, an aqueous caustic solution and an organic solvent with a minimal amount of DAC contaminants and unreacted monofunctional hydroxyaromatic compound. Such a process would allow production of a polycarbonate product having superior properties.

BRIEF SUMMARY OF THE INVENTION

The present invention relates to a method of preparing an aryl chloroformate of the formula I:

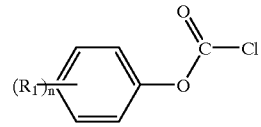

(I)

wherein n is an integer from 1 to 5, and $R_1$ represents hydrogen, a branched or unbranched alkyl group having from 1–15 carbon atoms, an aryl group which may be substituted or unsubstituted, a cycloaliphatic group which may be substituted or unsubstituted, or an arylalkyl group which may be substituted or unsubstituted, comprising the steps of:

A) introducing an aqueous caustic solution to a reaction vessel comprising a precharge solution, the precharge solution comprising
  1) from 0 to 100% of total input inert organic solvent;
  2) from 0 to 100% of total input monofunctional hydroxyaromatic compound of formula II, wherein n and $R_1$ in formula II has the same meaning as n and $R_1$ in formula I;

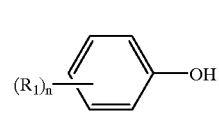

(II)

and 3) from 0 to 100% of total input phosgene, said precharge solution not including added water; and
B) simultaneously introducing
  1) a remaining portion of the total input monofunctional hydroxyaromatic compound; 2) a remaining portion of the total input phosgene; and 3) a remaining portion of total input inert organic solvent;
where a first overall molar ratio of phosgene to monofunctional hydroxyaromatic compound introduced into the reaction vessel is in a range of from about 1.25 to about 10 moles of phosgene per mole of monofunctional hydroxyaromatic compound introduced into the reaction vessel, and a second overall molar ratio of caustic to phosgene introduced in the reaction vessel is in a range of from about 0.6 to about 1.0 equivalents of caustic per mole of phosgene introduced into the reaction vessel,
steps A) and B) being conducted until a total monofunctional hydroxyaromatic compound level is reached or a desired ratio of phosgene to monofunctional hydroxyaromatic compound is reached,
and thereafter, maintaining the pH of the contents of the reaction vessel at a pH of from about 2 to about 5 for a period of time sufficient to stabilize the contents of the reaction vessel.

DETAILED DESCRIPTION OF THE INVENTION

The present invention may be understood more readily by reference to the following detailed description of the preferred embodiments of the invention and the examples included therein.

Before the present method and apparatus are disclosed and described, it is to be understood that this invention is not limited to specific systemic methods or to particular formulations, as such may, of course vary. It is also to be understood that the terminology used herein is for the purpose of describing particular embodiments only and is not intended to be limiting.

In this specification and in the claims which follow, reference will be made to a number of terms which shall be defined to have the following meaning.

The singular forms "a", "an" and "the" include plural referents unless the context clearly dictates otherwise.

The terms "aryl" and "hydroxyaromatic" are used interchangeably in the specification.

"Optional" or "optionally" mean that the subsequently described event or circumstance may or may not occur, and that the description includes instances where said event or circumstance occurs and instances where it does not.

"Overall molar ratio" is defined as the molar ratio of the total amount of the identified components introduced into a reaction system to form the desired product.

"Total input", as used herein, means the total amount, by weight, of the referenced component that is introduced into the reaction system.

A "remaining portion" as used herein, is the difference between the amount of a referenced component in the precharge solution and the total input of the referenced component.

Throughout this application, where publications are referenced, the disclosures of these publications are hereby incorporated by reference into this application in order to more fully describe the state of the art to which this invention pertains.

The present invention relates to a semi-batch process for the interfacial preparation of endcapping agents useful in polymer synthesis, the endcapping agents having the formula (I):

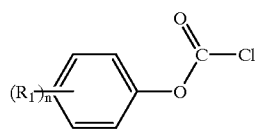

(I)

where n varies from 1 to 5, and $R_1$ represents hydrogen, a branched or unbranched alkyl group having from 1–15 carbon atoms, an aryl group which may be substituted or unsubstituted, a cycloaliphatic group which may be substituted or unsubstituted, or an arylalkyl group which may be substituted or unsubstituted. It is preferred than n is equal to 1 and that $R_1$ is present in the para position.

In a semi-batch process, an initial charge of materials is added to a reactor, after which one or more reactants and optionally solvents are added to the reactor during the course of the reaction. "Reaction system" as used herein means the vessel or reactor in which the reaction of the components takes place to form the monofunctional hydroxyaromatic chloroformate.

Endcapping agents produced by the method of the present invention include, but are not limited to, phenyl chloroformate, t-butyl phenyl chloroformate, p-cumyl phenyl chloroformate, chroman chloroformate, octyl phenyl or nonyl phenyl chloroformate, or a mixture thereof; more preferably phenyl chloroformate, p-cumyl phenylchloroformate, or a mixture thereof; even more preferably p-cumyl phenylchloroformate.

In the process as described herein, the production of hydroxyaromatic chloroformates is conducted in a semi-batch system by an interfacial process. The chloroformates are produced through the reaction of monofunctional aromatic compounds and carbonyl halides, in the presence of an aqueous caustic solution. The reaction is conducted in an inert organic solvent. Any suitable semi-batch reaction vessel or vessels may be used to contain the reaction system. The reaction vessel may include any feed, product removal, cooling and heating, and mixing attachments as are well known to the skilled worker.

Prior to introduction into the reactor system, the feed stream or streams introduced into the reaction vessel may optionally be mixed by suitable mixing means, such as in-line or static mixer. A mixing zone may be established before the reaction vessel, the reaction vessel may comprise a mixing zone, or both may be utilized.

The process conditions in the semi-batch reaction system may be varied, and generally any process conditions can be employed provided that the reaction between the carbonyl halide and the monofunctional hydroxyaromatic compound is allowed to proceed to produce the chloroformate product. It is preferable that the contents of the batch reaction vessel be maintained at a temperature of from about 5 to about 50° C., preferably from about 15 to about 20° C. during the process. The system pressure is preferably maintained at from about atmospheric pressure to about 150 psig.

While in the reaction vessel, the mixture comprising the inert organic solvent, monofunctional aromatic compound, and the aqueous caustic solution is agitated at a rate at least sufficient to prevent segregation of the aqueous and organic phases. If segregation occurs, the conversion of the reactants to the product will be reduced. The agitation of the aqueous and organic phase should be regulated such that the carbonyl halide is not wasted by increasing its hydrolysis rate, which occurs at excessively rapid agitation.

The applicants have surprisingly discovered that when using the method described herein, the final product consists of a solution of the desired hydroxyaromatic chloroformate in an organic solvent with an extremely low content of unreacted monofunctional hydroxyaromatic compound and DAC. The solution may be used directly in a polycarbonate synthesis reaction, or the hydroxyaromatic chloroformates may be easily separated from the solution by decantation, distillation or any suitable separation technique.

These results are achieved by the process of the invention, which comprises introducing an aqueous caustic solution comprising caustic into a reaction vessel which has been precharged with 0 to 100% by weight of total input organic solvent, 0 to 100% by weight of total input phosgene, and 0 to 100% by weight of total input monofunctional hydroxyaromatic compound. Simultaneously with the introduction of the aqueous caustic solution, a remaining portion of the total input organic solvent, a remaining portion of the total input phosgene, and a remaining portion of the total input monofunctional hydroxyaromatic compound are introduced into the reaction vessel.

The monofunctional hydroxyaromatic compound may be introduced into the reaction system as a solution, as a solid, as a melt, or a mixture thereof. In addition, the remaining portion of the monofunctional hydroxyaromatic compound introduced into the reaction vessel may be included in whole or in part in the remaining portion of the inert organic solvent stream introduced into the reaction vessel.

In the present invention, the reaction system is precharged with 1) from 0 to 100% by weight, preferably 50 to 100% by weight, even more preferably 70 to 80% by weight of total input inert organic solvent; 2) from 0 to 100% by weight, preferably 0 to 20% by weight, even more preferably 0 to 10% by weight of total input monofunctional hydroxyaromatic compound and 3) from 0 to 100% by weight, preferably 0 to 30% by weight, even more preferably 10 to 20% by weight of total input phosgene.

The phosgene, aqueous caustic solution, and monofunctional hydroxyaromatic compound are introduced into the reaction system in overall molar ratios which are based on ratios of the total input phosgene, aqueous caustic solution and monfunctional hdyroxyaromatic compound. By this process, hydrolysis of the carbonyl halide, such as phosgene, and the formation of undesired side products are minimized by employing a reaction procedure in which primary attention is given to maintaining the overall molar ratios of the reactants in the system, with only secondary attention being directed to pH.

In the present invention, it is critical that the overall molar ratios of the reactants which are introduced into the semi-batch vessel, are maintained within certain ranges in order to achieve the surprisingly low levels of DAC and unreacted monofunctional hydroxyaromatic compound. In particular, a first overall molar ratio of total input phosgene to total input monofunctional hydroxyaromatic compound introduced into the semi-batch vessel is in a first range of from about 1.25 to about 10 moles of phosgene per mole of monofunctional hydroxyaromatic compound introduced into the reaction vessel; preferably in the range of about 1.25 to about 4 moles of phosgene per mole of monofunctional hydroxyaromatic compound; even more preferably at a fixed molar rate ratio of from about 1.25 to about 3 moles of phosgene per mole of monofunctional hydroxyaromatic compound.

The second overall molar ratio of total input caustic to total input phosgene is in a second range of from about 0.6 to about 1.0 equivalents of caustic per mole of phosgene introduced into the reaction vessel, preferably the second overall molar ratio of total input caustic to total input phosgene is about 0.7 to about 0.9 equivalents of caustic per mole of phosgene introduced into the reaction vessel. The stated ranges in the specification are intended to include the enumerated endpoints.

Upon reaching a predetermined total monofunctional hydroxyaromatic compound level, or a desired ratio of monofunctional hydroxyaromatic compound, as defined above, the introduction of monofunctional hydroxyaromatic compound is terminated. This predetermined value of monofunctional hydroxyaromatic compound may be based, for example, on the amount of endcapping agent needed in a polycarbonate synthesis, which may differ depending on the desired molecular weight of the product. The final monofunctional hydroxyaromatic level is preferably in the range of about 2 to about 40 percent by weight, based on the weight of the organic phase.

In step b) of the process, which is conducted simultaneously with step a), a remaining portion of the total input inert organic solvent, total input phosgene, and total input monofunctional hydroxyaromatic compound is introduced into the reaction system. Optionally, the remaining portion, or a part of the remaining portion of the total monofunctional hydroxyaromatic compound may be dissolved in the remaining portion of the total input organic solvent. The contents of the reaction vessel are then maintained at a pH of from about 2 to about 5 for a period of time sufficient to stabilize the contents of the reaction vessel, preferably by the introduction of additional aqueous caustic solution. This step permits any unconverted hydroxyaromatic compound to be converted to the corresponding chloroformate, while minimizing the formation of any undesirable product, such as DAC. The period of time may be varied depending on the relative amounts of unreacted reactants, etc. In general, from about 5 to about 40 minutes is sufficient.

Optionally, water may be added before or at any point during the phosgenation or after phosgene input. This permits a more accurate pH reading; however, because water facilitates the hydrolysis of phosgene, it is preferable to add the water after about the midpoint of the monofunctional hydroxyaromatic compound addition, and more preferable to add the water after the end of phosgene addition.

Optionally, the reactor contents may be agitated while suspending the charging of components for a period of time during the steps of the process or between the steps of the process. Additionally, the reactants may be introduced into the reaction vessel continuously or in short pulses. It is preferable to introduce the reactants continuously.

The following discussion sets forth the reactants, including caustic, and solvents which are useful in the process of the invention. The particular components described are for illustrative purposes only, and the provided lists are not intended to be exhaustive.

Suitable monofunctional hydroxyaromatic compounds which may be used in the process of the present invention are represented by the general formula (II):

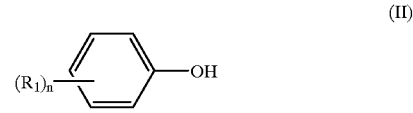

where n is an integer from 1 to 5, and wherein $R_1$ represents hydrogen, a branched or unbranched alkyl group having from 1–15 carbon atoms, an aryl group which may be substituted or unsubstituted, a cycloaliphatic group which may be substituted or unsubstituted, or an arylalkyl group which may be substituted or unsubstituted. It is preferred that n is equal to 1 and that $R_1$ is present in the para position.

Monofunctional hydroxyaromatic compounds as defined in formula (I) include, but are not limited to, phenol, p-tert-butylphenol, o-cresol, m-cresol, p-cresol, o-ethylphenol, p-ethylphenol, p-cumylphenol, chroman, p-octylphenol, p-nonylphenol, α-napthol, β-napthol and mixtures thereof. Preferred monofunctional hydroxyaromatic compounds are phenol, t-butyl phenol, p-cumyl phenol, chroman, and mixtures thereof; p-cumyl phenol is more preferred.

Suitable carbonyl halides for use in the present process, include, but are not limited to carbonyl chloride, carbonyl bromide, carbonyl iodide, carbonyl fluoride and mixtures thereof. Dimers of phosgene and trimers of phosgene are also suitable carbonyl halides. Phosgene is the preferred carbonyl halide. The carbonyl halide may be introduced into the reaction system in the form of a gas or a liquid, or it may be dissolved in any feed stream except the caustic feed stream before the introduction of the feed stream into the reaction system. It is therefore possible to prepare other haloformates, such as bromoformates, etc. by the process of the invention. Chloroformates are the most preferred.

Suitable organic solvents for use in the batch process include any organic solvent which is substantially insoluble in water and inert to the process conditions. The organic solvent should also be a liquid under the reaction conditions and should not react with the carbonyl halide, the hydroxyaromatic compound or the caustic. It is desirable that the hydroxyaromatic chloroformate product be soluble in the solvent. Suitable organic solvents include, but are not limited to aliphatic hydrocarbons such as hexane and heptane, aromatic hydrocarbons such as toluene, xylene, pentane, hexane, cyclohexane, and toluene; substituted aromatic hydrocarbons, such as chlorobenzene, dichlorobenzene, and nitrobenezene; chlorinated aliphatic hydrocarbons such as chloroform and methylene chloride, and mixtures of any of the aforementioned solvents. The aforementioned solvents may also be mixed with ethers, including but not limited to tetrahydrofuran. Chlorinated aliphatic hydrocarbons are preferred, in particular methylene chloride.

The reaction to produce the chloroformate requires an alkali metal base and/or an alkaline-earth metal base, herein referred to as a caustic. The caustic compound is preferably introduced as an aqueous solution comprising the alkali metal base and/or alkaline-earth metal base. The strength of the aqueous caustic solution may be varied, however it is preferable that the caustic compound comprise from about 10 wt % to about 50 wt % of the aqueous caustic solution.

Suitable alkali metal compounds which may be used as a caustic in the reaction system include, but are not limited to, sodium hydroxide, potassium hydroxide, lithium hydroxide, sodium hydrogen carbonate, potassium hydrogen carbonate, lithium hydrogen carbonate, sodium carbonate, potassium carbonate, lithium carbonate, sodium acetate, potassium acetate, lithium acetate, sodium stearate, potassium stearate, lithium stearate and mixtures thereof.

Suitable alkaline-earth metal compounds which may be used as a caustic in the reaction system include, but are not limited to, calcium hydroxide, barium hydroxide, magnesium hydroxide, strontium hydroxide, calcium hydrogen carbonate, barium hydrogen carbonate, magnesium hydrogen carbonate, strontium hydrogen carbonate, calcium carbonate, barium carbonate, magnesium carbonate, strontium carbonate, calcium acetate, barium acetate, magnesium acetate, strontium acetate, calcium stearate, barium stearate, magnesium stearate, strontium stearate and mixtures thereof.

EXAMPLES

The following examples are set forth to provide those of ordinary skill in the are with a complete description of how the compositions of matter and methods claimed herein are made and evaluated, and are not intended to limit the scope of what the inventors regard as their invention. Efforts have been made to insure accuracy with respect to numbers (e.g., amounts, temperature, etc.) but some errors and deviations should be accounted for. Unless indicated otherwise, parts are by weight, temperature is in ° C.

Example 1

A 2 liter glass vessel was configured with an agitator, pH electrode, cooling jacket and ports for continuous addition of phosgene, a methylene chloride solution of p-cumyl phenol (PCP), and an aqueous caustic solution. The vessel was precharged with 1200 ml of reagent grade methylene chloride. Chilled water glycol was circulated through the cooling jacket to maintain the temperature inside the vessel at 15–20° C. At time zero, phosgene gas was bubbled into the reactor for 2.5 minutes at a flow rate of 6 grams/minute. No NaOH solution was added during this interval. At time 2.5 minutes, two solutions were metered into the reactor 1) a solution of 106 grams (0.5 gram-mole) PCP in 300 ml methylene chloride (496 grams solution) was added at 40.4/grams minute and 2) a solution of 25 grams NaOH in 75 grams water was added at 8.12 grams/minute. During this time, phosgene was also added to the reactor at 6 grams/minute.

At time 14.8 minutes, the PCP solution addition was complete and both phosgene and NaOH solution were added at the previous rates for an additional 2.5 minutes. At 17.3 minutes, phosgene addition was terminated, and the NaOH solution was added under pH control to maintain a setpoint of 3. At 20 minutes, 100 ml of water was added to the reactor. At 27.3 minutes the batch was sampled and the product was found to have 596 ppm DAC and 3992 ppm residual PCP. The balance of the product was the desired product, p-cumyl phenylchloroformate.

Example 2

The test was repeated and the product contained 397 ppm DAC and 2577 ppm residual PCP.

Example 3

The reaction was conducted in essentially the same manner as Example 1 at a higher solids level. The vessel was initially charged with 1000 ml of methylene chloride, the PCP solution comprised 390 grams PCP and 405 grams of methylene chloride, and the PCP solution was added at 17.3 grams/minute. A total of 301.2 grams phosgene was added at 6 grams/minute. During PCP addition and for 2.5 minutes after the PCP solution addition was complete, a NaOH solution of 25 grams NaOH in 75 grams water was added at 8.12 grams/minute. The phosgenation was completed at 50.2 minutes, whereupon the NaOH solution was added under pH control to maintain a pH 3 setpoint until the final sample was taken. At 53 minutes, 100 ml of water was added. At 63 minutes, the final sample was taken and the product was analyzed to have 582 ppm DAC and 1655 ppm residual PCP. The balance was p-cumyl phenyl chloroformate. The methylene chloride phase contained 22.8% p-cumyl phenyl chloroformate.

Example 4

Example 1 was repeated with the addition of the 100 ml of water at the midpoint of PCP solution addition, rather than at 20 minutes. The sample for this reaction contained 444 ppm DAC, 1655 ppm residual PCP, and the balance p-cumyl phenyl chloroformate.

Example 5

A 1 liter reactor was fitted with a dual 2.5" 6-flat blade turbine agitator (450 rpm), a condenser, a phosgene addition dip tube, a NaOH addition dip tube, and a pH electrode in a recirculation loop. The reactor was charged with 600 ml of methylene chloride. The temperature was decreased to 15° C. and phosgene (29.0 grams, 0.29 moles) was added under modest agitation at 2.9 grams per minute over a 10 minute period. Phenol (3.456 grams, 0.037 moles) in 10 ml of methylene chloride was added via a syringe pump to the impeller tip over 2 minutes. A predetermined amount of 50 wt % sodium hydroxide (10.0 ml) based on NaOH to phosgene stoichiometry, was added to the reactor over about 5 minutes, and thereafter NaOH was added under pH control with a pH set point of 5. Temperature was controlled at 15 to 20° C. Samples at the end of the reaction were analyzed by HPLC and found to have no detectable DAC and 10,000 ppm phenol.

Comparative Example 1

A four liter reactor (similarly equipped to that of Example 1) was charged with 1320 ml of methylene chloride, 150 ml of water, and 36 grams of phosgene. At time zero, 133 grams of p-cumyl phenol dissolved on 330 ml of methylene chloride and an additional 36 grams of phosgene were charged to the reactor over a period of 35 minutes while the reactor temperature was maintained between 3 and 5° C. and the pH of the reaction was maintained between 4 and 6 by the addition of a 33 wt % solution of sodium hydroxide. At time 35 minutes, an additional 7.2 grams of phosgene were added over a period of two minutes, with 33 wt % sodium hydroxide addition to maintain the pH addition between 4 and 6. At time 52 minutes, the reaction was sampled and found to have 1600 ppm DAC and 4700 ppm residual PCP. The method for this example was taught by van Hout et al. in U.S. Pat. No. 5,399,657.

Comparative Example 2

Comparative Example 1 was repeated with the temperature maintained between 14 and 16° C. The product was found to have 3100 ppm DAC and 7100 ppm residual PCP.

Comparative Examples 1 and 2 demonstrate the importance of avoiding water in the formulation and adding caustic at a fixed ratio to phosgene, rather than adding caustic under pH control in order to minimize both the formation of DAC and residual p-cumyl phenol. Further, comparative example 2 shows that prior processes result in far higher DAC and residual p-cumyl phenol when operated in the temperature range reported in Example 1, which was according to the process of this invention. It is much more economical to operate at 15 to 20° C. than at 3 to 5° C.

The invention has been described in detail with particular reference to preferred embodiments thereof, but it will be understood that variations and modification can be effected within the scope of the invention.

Table I summarizes the results of the Examples described above. The symbol "t" designates time.

wherein n is an interger from 1 to 5, and $R_1$ represents hydrogen, a branched or unbranched alkyl group having from 1–15 carbon atoms, an aryl group, a cycloaliphatic group, or an arylalkyl group, comprising the steps of:
A) introducing an aqueous caustic solution to a reaction vessel comprising a precharge solution, the precharge solution comprising
1) from 0 to 100% of total input inert organic solvent;
2) from 0 to 100% of total input monofunctional hydroxyaromatic compound of formula II, wherein n and $R_1$ in formula II has the same meaning as n and $R_1$ in formula I;

(II)

and 3) from 0 to 100% of total input phosegene, said precharge solution not including added water; and
B) simultaneously introducing
1) a remaining portion of the total input monofunctional hydroxyaromatic compound; 2) a remaining portion of the total input phosgene; and 3) a remaining portion of total input inert organic solvent;
where a first overall molar ratio of phosgene to monofunctional hydroxyaromatic compound introduced into the reaction vessel is in a range of from about 1.25 to about 10 moles of phosgene per mole of monofunctional hydoxyaromatic compound introduced into the reaction vessel, and a second overall molar ratio of caustic to phosgene introduced in the reaction vessel is in a range of from about 0.6 to about 1.0 equivalents of caustic per mole of phosgene introduced into the reaction vessel,

TABLE I

| | Reaction Conditions | | | | MOLAR RATIO | | |
|---|---|---|---|---|---|---|---|
| | Precharge % COCl2 | Precharge % Phenolic | Precharge % CH2Cl2 | | | | |
| EXAMPLE | At t = 0 | At t = 0 | At t = 0 | NaOH:COCl2 | Phenolic: | COCl2 | NaOH |
| Example 1 | 14.5 | 0 | 80 | 0.71:1 | 1.00 | 2.10 | 1.50 |
| Example 2 | 14.5 | 0 | 80 | 0.71:1 | 1.00 | 2.10 | 1.50 |
| Example 3 | 5.0 | 0 | 77 | 0.81:1 | 1.00 | 1.65 | 1.34 |
| Example 4 | 5.0 | 0 | 77 | 0.81:1 | 1.00 | 1.65 | 1.34 |
| Example 5 | 100 | 100 | 100 | 0.66:1 | 1.00 | 7.97 | 5.17 |
| Comparative Ex. 1 | 45.5 | 0 | 80 | N/A (pH control) | 1.00 | 1.28 | N/A |
| Comparative Ex. 2 | 45.5 | 0 | 80 | N/A (pH control) | 1.00 | 1.28 | N/A |

What is claimed is:

1. A method of preparing an aryl chloroformate of the formula I:

(I)

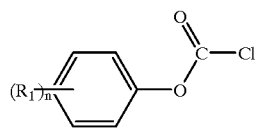

steps A) and B) being conducted until a total monofunctional hydroxyaromatic compound level is reached or a desired ratio of phosgene to onofunctional hydroxyaromatic compound is reached;

and thereafter, maintaining the pH of the contents of the reaction vessel at a pH of from about 2 to about 5 for a period of time sufficient to stabilize the contents of the reaction vessel.

2. The method of claim 1, wherein the precharge solution comprises from 50 to 100% by weight of the inert organic solvent.

3. The method of claim 1, wherein the precharge solution comprises from 80 to 100% by weight of the inert organic solvent.

4. The method of claim 1, wherein the remaining portion of the inert organic solvent contains the remaining portion of the monofunctional hydroxyaromatic compound.

5. The method of claim 1, wherein the precharge solution comprises 0 to 20% by weight of the monofunctional hydroxyaromatic compound.

6. The method of claim 1, wherein the precharge solution comprises 0 to 10% by weight of the monofunctional hydroxyaromatic compound.

7. The method of claim 1, wherein the precharge solution comprises from 0 to 30% by weight of the total input phosgene.

8. The method of claim 1, wherein the precharge solution comprises from 10 to 20% by weight of the total input phosgene.

9. The method of claim 1, further comprising the step of recovering the hydroxyaromatic chloroformate after maintaining the pH for a period of time sufficient to stabilize the contents of the reaction vessel.

10. The method of claim 1, wherein the monofunctional aromatic compound is phenol, p-tert-butylphenol, o-cresol, m-cresol, p-cresol, o-ethylphenol, p-ethylphenol, p-cumylphenol, chroman, p-octylphenol, p-nonylphenol, α-napthol, β-napthol or a mixture thereof.

11. The method of claim 1, wherein the monofunctional aromatic compound is p-cumyl phenol.

12. The method of claim 1, wherein the inert organic solvent is methylene chloride and the monofunctional aromatic compound is p-cumyl phenol.

13. The method of claim 1, wherein the aqueous caustic solution comprises sodium hydroxide.

14. The method of claim 1, wherein the contents of the reaction vessel are maintained at from about 15 to about 20° C.

15. The method of claim 1, further comprising the step of d) recovering the hydroxyaromatic chloroformate.

16. A method of preparing a polycarbonate, comprising the step of introducing the product solution of claim 1 into an interfacial polycarbonate synthesis.

17. A polycarbonate prepared by the method of claim 16.

18. The method of claim 1, wherein the pH of the contents of the reaction vessel is maintained at a pH for from about 2 to about 5 for a period of time sufficient to stabilize the contents of the reaction vessel by the addition of aqueous caustic solution.

19. A method of preparing an aryl chloroformate of the formula I:

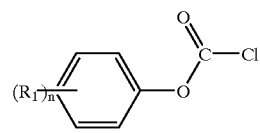

(I)

wherein n is an integer from 1 to 5, and $R_1$ represents hydrogen, a branched or unbranched alkyl group having from 1-15 carbon atoms, an aryl group, a cycloaliphatic group, or an arylalkyl group, comprising the steps of:

A) introducing an aqueous caustic solution to a reaction vessel comprising a precharge solution, the precharge solution comprising
   1) inert organic solvent,
   2) 100% of total input monofunctional hydroxyaromatic compound of formula II, wherein n and $R_1$ in formula II has the same meaning as n and $R_1$ in formula I,

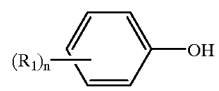

(II)

and 3) from 0 to 100% of total input phosgene, said precharge solution not including added water, and
B) introducing
   1) a remaining portion of the total input phosgene
where a first overall molar ratio of phosgene to monofunctional hydroxyaromatic compound introduced into the reaction vessel is in a range of from about 1.25 to about 10 moles of phosgene per mole of monofunctional hydroxyaromatic compound introduced into the reaction vessel, and a second overall molar ratio of caustic to phosgene introduced in the reaction vessel is in a range of from about 0.6 to about 1.0 equivalents of caustic per mole of phosgene introduced into the reaction vessel,
steps A) and B) being conducted until a desired ratio of phosgene to monofunctional hydroxyaromatic compound is reached,
and thereafter, maintaining the pH of the contents of the reaction vessel at a pH of from about 2 to about 5 for a period of time sufficient to stabilize the contents of the reaction vessel.

* * * * *